United States Patent
Koob et al.

(10) Patent No.: US 11,389,565 B2
(45) Date of Patent: *Jul. 19, 2022

(54) MOLDED PLACENTAL TISSUE COMPOSITIONS AND METHODS OF MAKING AND USING THE SAME

(71) Applicant: MiMedx Group, Inc., Marietta, GA (US)

(72) Inventors: Thomas J. Koob, Marietta, GA (US); Guilhem Denoziere, Marietta, GA (US); Rebeccah J. C. Brown, Marietta, GA (US)

(73) Assignee: MiMedx Group, Inc., Marietta, GA (US)

(*) Notice: Subject to any disclaimer, the term of this patent is extended or adjusted under 35 U.S.C. 154(b) by 418 days.

This patent is subject to a terminal disclaimer.

(21) Appl. No.: 15/984,600

(22) Filed: May 21, 2018

(65) Prior Publication Data

US 2018/0264171 A1 Sep. 20, 2018

Related U.S. Application Data (63) Continuation of application No. 13/815,753, filed on Mar. 15, 2013, now Pat. No. 10,029,030.

(51) Int. Cl.
*A61L 27/36* (2006.01)

(52) U.S. Cl.
CPC ....... *A61L 27/3604* (2013.01); *A61L 27/3695* (2013.01); *A61L 2400/06* (2013.01); *A61L 2430/34* (2013.01)

(58) Field of Classification Search
CPC ............. A61L 27/3604; A61L 27/3695; A61L 2400/06; A61L 2430/34
See application file for complete search history.

(56) References Cited

U.S. PATENT DOCUMENTS

| | | |
|---|---|---|
| 2,694,914 A | 11/1954 | Glover, Jr. |
| 3,272,204 A | 9/1966 | Artandi |
| 4,564,368 A | 1/1986 | Sawyer et al. |
| 4,703,108 A | 10/1987 | Silver et al. |
| 4,745,771 A | 5/1988 | Linner et al. |
| 4,847,049 A | 7/1989 | Yamamoto |
| 4,968,325 A | 11/1990 | Black et al. |
| 5,118,867 A | 6/1992 | Bahrmann et al. |

(Continued)

FOREIGN PATENT DOCUMENTS

| | | |
|---|---|---|
| CN | 101433556 A | 5/2009 |
| EP | 431164 A1 | 6/1991 |

(Continued)

OTHER PUBLICATIONS

Office Action for Japanese Application No. 2016-502950 dated Jan. 22, 2019.

(Continued)

*Primary Examiner* — David W Berke-Schlessel
*Assistant Examiner* — Trent R Clarke
(74) *Attorney, Agent, or Firm* — Alston & Bird LLP (57) ABSTRACT

Described herein are molded dehydrated placental tissue compositions, and pharmaceutical compositions thereof. The compositions have numerous medical applications. Methods for making and using the molded dehydrated placental tissue compositions are also described herein.

11 Claims, 1 Drawing Sheet

(56) References Cited

U.S. PATENT DOCUMENTS

| | | |
|---|---|---|
| 5,284,655 A | 2/1994 | Bogdansky et al. |
| 5,541,232 A | 7/1996 | Howell et al. |
| 5,807,581 A | 9/1998 | Rosenblatt et al. |
| 6,030,635 A | 2/2000 | Gertzman et al. |
| 6,129,757 A | 10/2000 | Weadock |
| 6,166,184 A | 12/2000 | Hendriks et al. |
| 6,387,369 B1 | 5/2002 | Pittenger et al. |
| 6,503,244 B2 | 1/2003 | Hayman |
| 6,565,960 B2 | 5/2003 | Koob et al. |
| 6,716,895 B1 | 4/2004 | Terry |
| 6,821,530 B2 | 11/2004 | Koob et al. |
| 6,893,462 B2 | 5/2005 | Buskirk et al. |
| 6,936,271 B1 | 8/2005 | Oliver et al. |
| 7,101,857 B2 | 9/2006 | Sung et al. |
| 7,311,904 B2 | 12/2007 | Hariri |
| 7,311,905 B2 | 12/2007 | Hariri |
| 7,901,455 B2 | 3/2011 | Koob et al. |
| 8,067,044 B2 | 11/2011 | Henry et al. |
| 8,177,839 B2 | 5/2012 | Koob et al. |
| 8,192,481 B2 | 6/2012 | King |
| 8,323,701 B2 | 12/2012 | Daniel et al. |
| 8,357,403 B2 | 1/2013 | Daniel et al. |
| 8,367,148 B2 | 2/2013 | Greenhalgh et al. |
| 8,372,439 B2 | 2/2013 | Daniel et al. |
| 8,623,421 B2 | 1/2014 | Daniel |
| 8,904,664 B2 | 12/2014 | Pringle et al. |
| 2002/0019516 A1 | 2/2002 | Noff et al. |
| 2002/0028243 A1* | 3/2002 | Masters ............... A61P 17/02 424/484 |
| 2002/0037940 A1 | 3/2002 | Koob et al. |
| 2002/0123141 A1 | 9/2002 | Hariri |
| 2002/0160510 A1 | 10/2002 | Hariri |
| 2003/0007991 A1* | 1/2003 | Masters ............... A61L 27/34 424/423 |
| 2003/0032179 A1 | 2/2003 | Hariri |
| 2003/0187515 A1 | 10/2003 | Hariri |
| 2003/0204023 A1 | 10/2003 | Koob et al. |
| 2004/0028711 A1 | 2/2004 | Uchida et al. |
| 2004/0048796 A1 | 3/2004 | Hariri et al. |
| 2005/0142161 A1 | 6/2005 | Freeman et al. |
| 2005/0147690 A1* | 7/2005 | Masters ............... A61K 9/1658 424/499 |
| 2005/0163817 A1* | 7/2005 | Masters ............... A61L 27/227 424/423 |
| 2005/0196440 A1* | 9/2005 | Masters ............... A61K 38/38 424/464 |
| 2006/0073207 A1* | 4/2006 | Masters ............... A61K 38/39 424/488 |
| 2006/0140913 A1 | 6/2006 | Bhatia |
| 2006/0166361 A1 | 7/2006 | Seyda et al. |
| 2006/0210532 A1 | 9/2006 | Carmeliet et al. |
| 2007/0020225 A1 | 1/2007 | Abramson et al. |
| 2007/0021762 A1 | 1/2007 | Liu et al. |
| 2007/0071740 A1 | 3/2007 | Tseng et al. |
| 2007/0071828 A1 | 3/2007 | Tseng et al. |
| 2007/0160573 A1 | 7/2007 | Gengrinovitch |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0050347 A1 | 2/2008 | Ichim |
| 2008/0069895 A1 | 3/2008 | Liu et al. |
| 2008/0131966 A1 | 6/2008 | Hariri |
| 2008/0161917 A1 | 7/2008 | Koob et al. |
| 2008/0181935 A1 | 7/2008 | Bhatia et al. |
| 2008/0181967 A1 | 7/2008 | Liu et al. |
| 2008/0200992 A1 | 8/2008 | Koob et al. |
| 2008/0233552 A1 | 9/2008 | Ma et al. |
| 2009/0012629 A1 | 1/2009 | Yao et al. |
| 2009/0036996 A1 | 2/2009 | Roeber |
| 2009/0053290 A1 | 2/2009 | Sand et al. |
| 2009/0092664 A1 | 4/2009 | Mumper et al. |
| 2009/0142831 A1 | 6/2009 | Hariri |
| 2009/0216233 A1 | 8/2009 | Wiedrich et al. |
| 2009/0287308 A1 | 11/2009 | Davis et al. |
| 2009/0291891 A1 | 11/2009 | Neufeld |
| 2010/0028849 A1 | 2/2010 | Shelby et al. |
| 2010/0094318 A1 | 4/2010 | Li et al. |
| 2010/0094404 A1 | 4/2010 | Greenhalgh et al. |
| 2010/0104539 A1 | 4/2010 | Daniel et al. |
| 2010/0136114 A1 | 6/2010 | Mao |
| 2010/0143312 A1 | 6/2010 | Hariri et al. |
| 2010/0143487 A1* | 6/2010 | Masters ............... A61K 9/0019 424/499 |
| 2010/0178297 A1 | 7/2010 | Carmeliet et al. |
| 2010/0209408 A1 | 8/2010 | Stephen A. et al. |
| 2010/0260847 A1 | 10/2010 | Hariri |
| 2010/0272782 A1 | 10/2010 | Owens et al. |
| 2010/0291182 A1 | 11/2010 | Palasis et al. |
| 2010/0317677 A1 | 12/2010 | Hassel et al. |
| 2011/0044997 A1 | 2/2011 | Rankin et al. |
| 2011/0097379 A1 | 4/2011 | Yoo et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0282448 A1 | 11/2011 | Paulos et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0041539 A1* | 2/2012 | Masters ............... A61L 27/507 623/1.13 |
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0202676 A1 | 8/2013 | Koob et al. |
| 2013/0218274 A1 | 8/2013 | Spencer et al. |
| 2013/0230561 A1 | 9/2013 | Daniel et al. |
| 2013/0273008 A1 | 10/2013 | Lemper et al. |
| 2013/0344162 A1 | 12/2013 | Morse et al. |
| 2014/0017280 A1 | 1/2014 | Daniel et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0067068 A1 | 3/2014 | Koob et al. |
| 2014/0106447 A1 | 4/2014 | Brown et al. |
| 2014/0140964 A1 | 5/2014 | Brown et al. |
| 2014/0142025 A1 | 5/2014 | Koob |
| 2014/0142041 A1 | 5/2014 | Koob |
| 2014/0205646 A1 | 7/2014 | Morse et al. |
| 2014/0271728 A1 | 9/2014 | Koob et al. |
| 2014/0308233 A1 | 10/2014 | Koob |
| 2014/0342015 A1 | 11/2014 | Murphy et al. |
| 2014/0356451 A1 | 12/2014 | Koob |

FOREIGN PATENT DOCUMENTS

| | | |
|---|---|---|
| EP | 0431479 A1 | 6/1991 |
| EP | 0 506 207 B1 | 9/1992 |
| JP | 2002-508673 A | 3/2002 |
| JP | 2004-535244 A | 11/2004 |
| JP | 2006-519681 A | 8/2006 |
| JP | 2004-532714 A | 3/2010 |
| KR | 10/1991/0011272 | 8/1991 |
| KR | 10/1991/0011727 A | 8/1991 |
| KR | 2001100588 A | 11/2001 |
| WO | WO-87/00062 A1 | 1/1987 |
| WO | WO-88/03805 A1 | 6/1988 |
| WO | WO-01/00151 A1 | 1/2001 |
| WO | WO-01/08716 A1 | 2/2001 |
| WO | WO-2004/026244 | 4/2004 |
| WO | WO-2005/017165 | 2/2005 |
| WO | WO-2007/010305 | 1/2007 |
| WO | WO-2007/076522 | 7/2007 |
| WO | WO-2007/083984 A1 | 7/2007 |
| WO | WO-2009/033160 A1 | 3/2009 |
| WO | WO-2009/048908 | 4/2009 |
| WO | WO-2009/132186 A1 | 10/2009 |
| WO | WO-2010/029344 A2 | 3/2010 |
| WO | WO-2011/103470 | 8/2011 |

(56) References Cited

FOREIGN PATENT DOCUMENTS

| WO | WO-2011/127117 | | 10/2011 |
|---|---|---|---|
| WO | WO-2012/003377 | | 1/2012 |
| WO | WO-2012/065937 | A1 | 5/2012 |
| WO | WO-2012/069558 | A1 | 5/2012 |
| WO | WO-2012/069559 | A1 | 5/2012 |
| WO | WO-2012/112410 | A2 | 8/2012 |
| WO | WO-2012/112417 | A2 | 8/2012 |
| WO | WO-2012/112441 | A1 | 8/2012 |
| WO | WO-2013/095830 | A1 | 6/2013 |

OTHER PUBLICATIONS

U.S. Appl. No. 13/815,753, filed Mar. 15, 2013, 10,029,030.
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Borkow et al., "Reducing the risk of skin pathologies in diabetics by using copper impregnated socks", Medical Hypotheses, 2009, 1-4, doi:10.1016/j.mehy.2009.02.050.
Derwent Abstract for KR 200110588, original document published Nov. 2001.
EpiFix Product Brochure (2011).
Extended European Search Report dated Dec. 2, 2014, for European Patent Application No. EP 12746721.
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Kelly et al., "Disparate Effects of Similar Phenolic Phytochemicals as Inhibitors of Oxidative Damage to Cellular DNA", Mutation Res., vol. 485, pp. 309-318, (2001).
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Konishi et al., In vivo anti-tumor effect through the controlled release of cisplatin from biodegradable gelatin hydrogel,: J. Controlled Release, (2003), 92(3):301-313.
Koob et al., "Biological properties of dehydrated human amnion-chorion composite graft: implications for chronic wound healing", International Wound Healing, 10(5):493-500 (2013).
Koob et al., "Mechanical and thermal properties of novel polymerized NDGA013gelatin hydrogels", Biomaterials, (2003), 24(7):1285-1292.
Koob et al., Material properties of polymerized NDGA-collagen composite fibers: Development of biologically based tendon constructs. Biomaterials, 23(1): 203-212, 2002.
Kostova, "Platinum Complexes as Anticancer Agents", Recent Patents on Anti-Cancer Drug Discovery, 2006; 1(1):1-22.
Lu, et al., "Molecular mechanisms and clinical applications of nordihydroguaiaretic acid (NDGA) and its derivatives: An update," Med. Sci. Monit., (2010), 16(5):RA93-RA100.
Matfield et al., "Watertight closure of spinal dura mater: Technical note," J. Neurosurg., (1975), 43(5):639-640.
"MiMedx Group Announces Launch of EpiFixTM and Hiring of Vice President, Wound Care," Mimedx Press Release (2011).
MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers," Biotechnology Progress, (2007), 23(4):990-994.
Nagaya et al., "Transplantation of mesenchymal stem cells improves cardiac function in a rat model of dilated cardiomyopathy", Circulation, 112(8):1128-1135 (2005).
Parolini et al., "Toward cell therapy using placenta-derived cells: disease mechanisms, cell biology, preclinical studies, and regulatory aspects at the round table", Stem Cells and Development, 19(2):143-154 (2010).
PCT International Preliminary Report of Patentability dated Feb. 17, 2015 for PCT Application No. PCT/US2013/054320.
PCT International Preliminary Report of Patentability for PCT Application No. PCT/US14/28975 dated Feb. 6, 2015.
PCT International Preliminary Report of Patentibility for PCT Patent Application PCT/US2013/063736, dated Sep. 25, 2014.
PCT International Preliminary Report of Patentibility for PCT Patent Application PCT/US2013/064146, dated Sep. 25, 2014.
PCT International Preliminary Report on Patentability dated Dec. 3, 2014 for PCT Patent Application No. PCT/US2013/067618.
PCT International Preliminary Report on Patentability dated Dec. 30, 2014 for PCT Patent Application No. PCT/US13/67622.
PCT International Preliminary Report on Patentability dated Dec. 30, 2014, for International Patent Application No. PCT/US2013/063736.
PCT International Preliminary Report on Patentability dated Dec. 8, 2014, for International Patent Application No. PCT/US2013/054322.
PCT International Preliminary Report on Patentability dated Feb. 14, 2013 for PCT Patent Application No. PCT/US2012/024814.
PCT International Preliminary Report on Patentability dated Jan. 16, 2014 in related PCT Patent Application No. PCT/US12/66862.
PCT International Preliminary Report on Patentability dated Nov. 10, 2014 for PCT Patent Application No. PCT/US2013/067623.
PCT International Preliminary Report on Patentability dated Nov. 27, 2014, for International Patent Application No. PCT/US2013/055003.
PCT International Preliminary Report on Patentability dated Nov. 28, 2014, for International Patent Application No. PCT/US2013/054319.
PCT International Preliminary Report on Patentability for PCT Application No. PCT/US2012/024798, dated Feb. 1, 2013.
PCT International Search Report and Written Opinion dated Apr. 13, 2015 for PCT Patent Application No. PCT/US15/12087.
PCT International Search Report and Written Opinion dated Apr. 16, 2014 for PCT Patent Application No. PCT/US13/67622.
PCT International Search Report and Written Opinion dated Apr. 21, 2014 for PCT Patent Application No. PCT/US13/67623.
PCT International Search Report and Written Opinion dated Apr. 22, 2014 for PCT Patent Application No. PCT/US13/67618.
PCT International Search Report and Written Opinion dated Apr. 22, 2014 for PCT Patent Application No. PCT/US13/67620.
PCT International Search Report and Written Opinion dated Aug. 26, 2014 for PCT Patent Application No. PCT/US2014/033346.
PCT International Search Report and Written Opinion dated Dec. 29, 2014 for PCT Patent Application No. PCT/US2014/053270.
PCT International Search Report and Written Opinion dated Dec. 30, 2014 in PCT Patent Application No. PTC/US2014/054603.
PCT International Search Report and Written Opinion dated Jan. 9, 2014 for PCT Patent Application No. PCT/US2013/064146.
PCT International Search Report and Written Opinion dated Jul. 24, 2014 for PCT Patent Application No. PCT/US2014/028975.
PCT International Search Report and Written Opinion dated Jun. 20, 2012 for PCT Patent Application No. PCT/US12/24798.
PCT International Search Report and Written Opinion dated Oct. 22, 2013 for PCT Patent Application No. PCT/US2013/054322.
PCT International Search Report and Written Opinion for PCT Patent Appl. PCT/US2014/012141, dated May 20, 2014.
PCT International Search Report and Written Opinion for PCT Patent Application No. PCT/US2012/065672, dated Feb. 8, 2013.
PCT International Search Report and Written Opinion for PCT Patent Application No. PCT/US2013/054322, dated Oct. 22, 2013.
PCT International Search Report and Written Opinion for PCT Patent Application No. PCT/US2012/66862, dated Feb. 12, 2013.
PCT International Search Report and Written Opinion for PCT Patent Application No. PCT/US2013/054319, dated Nov. 13, 2013.
PCT International Search Report and Written Opinion for PCT Application No. PCT/US2013/054320, dated Nov. 6, 2013.

(56) References Cited

OTHER PUBLICATIONS

PCT International Search Report and Written Opinion for PCT Application No. PCT/US2013/054325, dated Oct. 28, 2013.
PCT International Search Report and Written Opinion for PCT Application No. PCT/US2013/055003, dated Nov. 19, 2013.
PCT International Search Report and Written Opinion for PCT Patent Application No. PCT/US2012/024814 dated Aug. 16, 2012.
PCT International Search Report: and Written Opinion for PCT Appl. PCT/US13/63736, dated Aug. 12, 2014.
Proxy Biomedical, "Vitamesh", http://proxybiomedical,comiImages/ML005-01-Rev002.pdf (accessed on Jun. 5, 2014).
Tao et al., "Implantation of amniotic membrane to reduce postlaminectomy epidural adhesions," Eur. Spine. J., 18:1202-1212, (2009).
Toda, et al., "The potential of amniotic membrane/amnion-derived cells for regeneration of various tissues," Journal of Pharmacological Sciences, 105:215-228, (2007).
European Application No. 18154692.0, Article 94(3) Communication dated Oct. 24, 2019.
Office Action for Japanese Application No. 2016-502950 dated Dec. 13, 2017.

\* cited by examiner

MOLDED PLACENTAL TISSUE COMPOSITIONS AND METHODS OF MAKING AND USING THE SAME

CROSS-REFERENCE TO RELATED APPLICATIONS

This application is a continuation of U.S. patent application Ser. No. 13/815,753, filed Mar. 15, 2013, which is incorporated herein by reference in its entirety.

BACKGROUND OF THE INVENTION

Field of the Invention

This invention is directed to molded dehydrated placental tissue and, in particular, to molded dehydrated placental tissue compositions. Such compositions are prepared from dehydrated micronized placental tissue. This invention also includes methods of making and using such compositions.

State of the Art

Placental tissue is known in the art as a basis for wound coverings and wound healing. Typically, the placental tissue is harvested after an elective Cesarean surgery. The placenta is composed of an amniotic membrane which has two primary layers of tissue, amnion and chorion. Amnion tissue is the innermost layer of the amniotic sac and in direct contact with the amniotic fluid. The amniotic sac contains the amniotic fluid and protects the fetal environment. Histological evaluation indicates that the membrane layers of the amnion consist of a single layer of epithelium cells, thin reticular fibers (basement membrane), a thick compact layer, and a fibroblast layer. The fibrous layer of amnion (i.e., the basement membrane) contains collagen types IV, V, and VII, and cell-adhesion bio-active factors including fibronectin and laminins. Heretofore, wound covering or wound healing compositions comprising placental tissue components typically were in the form of grafts wherein individual layers such as the amnion and/or chorion layer formed a discreet component of the graft.

While such tissue grafts provide significant medical benefits, these grafts are very thin and lack sufficient structural competency to accord for non-invasive means for insertion into an internal organ or body part of a patient.

Described herein is a unique approach wherein dehydrated micronized placental tissue component(s) are molded into shapes and sizes which can be non-invasively introduced into or onto a patient for the purposes of wound healing and other medical applications.

SUMMARY OF THE INVENTION

This invention is directed, in part, to the discovery that compositions composed of molded, dehydrated micronized placental component(s), and pharmaceutical compositions thereof impart significant benefits when used alone or as part of a wound covering or implant. Accordingly, these compositions comprising molded dehydrated micronized placental components have numerous medical applications.

In one aspect, the invention relates to a molded, dehydrated, placental tissue composition having a defined size and shape. The composition comprises one or more placental tissue components such as amnion, chorion, intermediate tissue layer, and any combination thereof. The placental tissue compositions of this invention have a sufficient density and cohesiveness to maintain their size and shape at least until the molded, dehydrated placental tissue compositions are introduced into a subject.

In one embodiment, the density of the molded placental tissue composition is sufficient such that the placental tissue component can be formed into any desired shape and the molded placental tissue composition will maintain its shape during introduction into a subject. For example, the density of the placental tissue composition is in a range from at least about 1.2 g/cm$^3$ to about 10 g/cm$^3$. Such molded placental tissue compositions can be introduced non-invasively into the patient as described herein below or can be introduced by conventional invasive means. This permits the attending clinician significant flexibility in treating the patient taking into account the purpose of the treatment, the age and condition of the patient, and other factors well within the skill of the art.

In another embodiment, the molded, dehydrated placental tissue composition is sufficiently cohesive such that the placental tissue composition does not break, splinter, disintegrate or fragment during introduction into a subject. The suitable density and cohesive mass can be determined by one skilled in the art based on the purpose for introduction, the amount of placental tissue composition to be used, the manner of administration/introduction, and the specific body part for administration. The desired shape of the molded, dehydrated placental tissue composition is maintained at least until introduction into a subject.

The molded, dehydrated placental tissue composition is designed to erode after introduction wherein the period for erosion is defined by the density and degree of cohesiveness of the molded, dehydrated placental tissue as well as its size. During erosion, growth factors and other biological factors are released over time from the placental tissue thereby providing for sustained release of such factors at the location of administration/introduction.

In a related aspect, the molded, dehydrated placental tissue composition with a defined size and shape is obtained by compressing at least one of dehydrated micronized placental tissue component or any combination thereof under a suitable compressive pressure, e.g., a pressure ranging from 1 to 5000 MPa, for a defined period of time, e.g., from 10 seconds to 10 minutes, or longer, such that the obtained placental tissue will possess sufficient density and cohesive mass to maintain its size and shape at least until administered or implemented.

Prior to compression, the micronized placental component(s) are dehydrated to the extent that compression can be performed in a non-porous mold. In other words, the water content in the dehydrated micronized placental components is sufficiently low that compression to form the compositions of this invention can be conducted in a non-porous mold. For instance, the water content of the dehydrated micronized placental components is preferably less than about 20%, less than about 15%, less than about 10%, or less than about 5%.

It is within the purview of one of ordinary skill in the art to use a suitable means to compress at least one of micronized amnion, chorion, intermediate tissue layer, and any combination thereof. For instance, the micronized placental tissue may be compressed through use of a mold of any desired size and shape to obtain the desired size and shape.

It is within the purview of one skilled in the art to choose any molding technique where the dehydrated micronized placental component(s) are loaded into a shaped mold and subjected to a pressure such that the placental tissue composition takes the shape of the mold following compression.

The molded placental tissue composition can take any desired shape, such as the shapes of pins, nails, barrels, rivets, darts, membranes. In certain embodiments, the resulting molded, dehydrated placental tissue composition can have a hollow center or voids in the graft. Voids in the composition can be achieved by use of a laser to induce channels into or through the composition. One skilled in the art would understand that once the molded placental tissue composition is formed, it can be subjected to post-formation treatment, such as cavitation by laser drilling, to increase the surface area of the placental, tissue composition.

In one embodiment, the compression of dehydrated micronized placental components is carried out under controlled temperature to minimize denature of proteins, growth factors and other biological factors contained in placental tissue. As molding often raises the temperature within the mold, a heat sink can be employed in conjunction with the molding process to control the temperature increase.

This invention is also directed to methods for making and using molded placental tissue compositions.

Several of the advantages of this invention are set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWING

The accompanying drawing, which is incorporated in and constitutes a part of this specification, illustrates several aspects described below.

DETAILED DESCRIPTION

Figure 1:
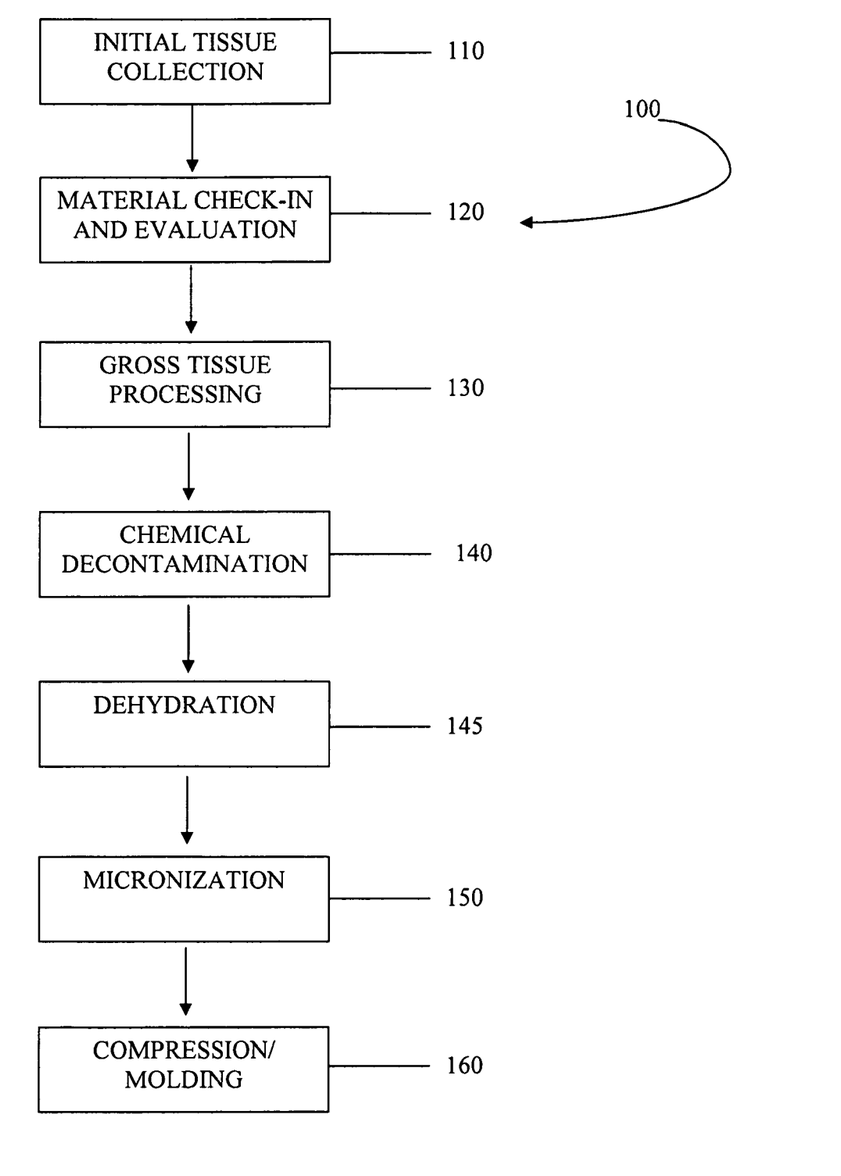
The FIGURE is an overview flow chart of the process for making the molded, dehydrated placental tissue composition described herein.

Before the present invention is disclosed and described, it is to be understood that the aspects described below are not limited to specific compositions, methods or preparing such compositions, or uses thereof as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism including but not limited to mammalian subjects such as humans, farm animals, domesticated pets and the like.

The term "amnion" as used herein includes amniotic membrane where the intermediate tissue layer is intact or has been substantially removed.

The term "placental tissue" refers to any and all of the well known components of the placenta including but not limited to amnion, chorion, Wharton's Jelly, and the like. In one preferred embodiment, the placental tissue does not include any of the umbilical cord components (e.g., Wharton's jelly, umbilical cord vein and artery, and surrounding membrane).

The term "mold," "molded," or "molding" includes any form of molding such as the use of actual molds, extrusion under pressure, stamping or any pressurized method, and the like such that micronized placental tissue components, such as amnion, chorion, intermediate tissue layer, and any combination thereof, are compressed under pressure to produce a placental tissue composition that has a defined size and shape for a defined period of time for use either ex vivo or in vivo. The molded placental tissue composition has a sufficient density and cohesiveness to maintain its size and shape.

Titles or subtitles may be used in the specification for the convenience of a reader, which are not intended to influence the scope of the present invention. Additionally, some terms used in this specification are more specifically defined below.

I. Compositions Comprising Molded Dehydrated Micronized Placental Components

Described herein are molded dehydrated placental compositions and pharmaceutical compositions thereof. Such compositions are prepared from micronized placental tissue components, which are described in PCT Application No. PCT/US12/24798, as well as in U.S. provisional application Ser. Nos. 61/442,346, 61/543,995, and 61/683,700. The contents of these applications are specifically incorporated by reference in their entireties. It is understood that the term "micronized" is meant to include micron and sub-micron sized placental tissue particles.

In one aspect, the invention is directed to a composition that includes (a) molded dehydrated placental tissue comprising at least one of micronized amnion, chorion, intermediate tissue layer, or any combination thereof and optionally (b) a pharmaceutically acceptable excipient.

For example, the composition includes molded, dehydrated placental tissue which can be used without the addition of any fillers, stabilizers, buffers, or pharmaceutical components. Alternatively, the composition includes molded, dehydrated placental tissue and at least one pharmaceutical excipient such as a filler, a stabilizer, a buffer, a coloring agent, a disintegrating agent and the like and optionally one or more pharmaceutical components. Preferably, the coloring agent facilitates in locating and properly placing the placental tissue, which is otherwise almost transparent, to the intended treatment site. The disintegrating agent modifies the rate that the molded dehydrated placental tissue composition erodes or disintegrates in vivo after being introduced to a subject.

The compositions preferably comprise micronized amnion and chorion. In yet another aspect, the composition includes molded, dehydrated placental tissue comprising micronized amnion. In yet another aspect, the composition includes molded, dehydrated placental tissue comprising micronized amnion, which epithelium layer is substantially removed from amnion.

As one of ordinary skill in the art would understand, the molded, dehydrated placental tissue composition of the invention is compressed under pressure into any shape or size, as long as the molded placental tissue composition has a coherent mass having a certain density.

Alternatively, the dehydrated micronized placental components are compressed into any mold having a desired shape or size such that the molded dehydrated placental tissue graft takes the shape and size of the mold. It is within the purview of one of ordinary skill in the art to select suitable molding material, such as silicone, resin, Teflon®, or stainless steel, to form a mold of desired shape and size.

Advantageously, the molded, dehydrated placental tissue composition described herein has low water resorbability such that the shape of the placental tissue composition is maintained at least through the period of introduction into the patient and preferably for a defined period of time in vivo following introduction to a subject. It is understood that the placental tissue composition erodes in vivo and releases the growth factors and other biological factors contained in the placental tissue. Thus, the retention of the shape of the molded, dehydrated placental tissue composition means that the overall shape is retained even if that shape is subject to or initiates erosion.

II. Methods of Making Compositions Comprising Molded Dehydrated Micronized Placental Components The FIGURE depicts an overview (100) and certain aspects of the steps to harvest, process, and prepare molded dehydrated micronized placental material. More detailed descriptions and discussion regarding each individual step will follow. Initially, the placental tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140) and dehydrated (step 145). After decontamination and dehydration, the placental tissue components (e.g., amnion, intermediate tissue layer and/or chorion individually or as grafts) are then micronized (step 150). The micronized placental components are compressed/molded under pressure into a desired shape or size (step 160). Each step is described in detail below.

Initial Tissue Collection (Step 110)

The components used to produce the molded, dehydrated placental tissue composition described herein are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is preferably collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below.

In certain aspects, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed. Here, fibroblast cells are present in the fibroblast layer.

When the placental tissue is Wharton's jelly, the following exemplary procedure can be used. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion is removed from the Wharton's jelly by cutting the amnion. Here, the outer membrane of the umbilical cord is removed such that Wharton's jelly is the only remaining component. Thus, the Wharton's jelly as used herein does not include the outer umbilical cord membrane and umbilical cord vessels. The Wharton's jelly can be cut into strips. In one aspect, the strips are approximately 1-4 cm by 10-30 cm with an approximate thickness of 1.25 cm; however, other thicknesses are possible depending on the application.

Chemical Decontamination (Step 140)

The placental tissue can be chemically decontaminated using the techniques described below. In one aspect, the amnion is decontaminated at room temperature. In one aspect, the amnion produced in step 130 (e.g., with or without the intermediate tissue layer) can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

The following exemplary procedure can be used when the placental tissue is Wharton's jelly. The Wharton's jelly is transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) with 18% NaCl. The container is sealed and placed on rocker plate and agitated for 60 to 90 minutes.

After the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1° C. to 10° C. for up to 24 hours.

The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After incubation, the jar is returned to the sterile field. The Wharton's jelly should have a cream white visual appearance with no evidence of brownish discoloration.

Dehydration (Step 145)

In one aspect, the placental tissue or components thereof as described above, or any combination thereof can be processed into tissue grafts (i.e., laminates) that are subsequently micronized. In another aspect, the placental tissue or individual components thereof can be dehydrated independently and subsequently micronized alone or as a mixture of components. In one aspect, the tissue (i.e., individual membrane or graft) is dehydrated by chemical dehydration followed by freeze-drying. In one aspect, the chemical dehydration step is performed by contacting the amnion, chorion, and/or intermediate layer with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue is freeze-dried in order to remove any residual water and polar organic solvent. In one aspect, the amnion, chorion, and/or intermediate layer can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon® or of Delrin®, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Once the tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the tissue. In one aspect, the amnion, chorion, and/or intermediate layer is laid on a suitable drying fixture (either as individual strips or as a laminate discussed above), and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45° C. to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

In one aspect, the placental tissue can be dehydrated using a dehydration device which enhances the rate and uniformity of the dehydration process. Representative dehydration device suitable for drying placental tissue grafts are described in U.S. Provisional Patent Application No. 61/683,700, filed on Aug. 15, 2012, and in U.S. patent application Ser. No. 13/744,332, filed on Jan. 17, 2013. The contents of these applications are incorporated by reference in their entireties.

Preparation of Micronized Placental Components
(Step 150)

Once the placental tissue or components thereof as described above have been dehydrated individually or in the form of tissue graft, the dehydrated tissue(s) is micronized. The micronized placental components can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 less than 400 less than 300 µm, less than 200 µm, less than 100 µm, less than 50 µm, less than 25 µm, less than 20 µm, less than 15 µm, less than 10 µm, less than 9 µm, less than 8 µm, less than 7 µm, less than 6 µm, less than 5 µm, less than 4 µm, less than 3 µm, less than 2 µm, or from 2 µm, to 400 µm, from 25 µm to 300 µm, from 25 µm to 200 µm, or from 25 µm to 150 µm. In one aspect, the micronized composition has particles that have a diameter less than 150 µm, less than 100 µm, or less than 50 µm. In other aspects, particles having a larger diameter (e.g. 150 µm to 350 µm) are desirable. In all cases, the diameter of the particle is measured along its longest axis.

In one embodiment, the size of the particles may be reduced to nano-range. As one skilled in the art would understand, nanoparticles of placental components may be desirable for the increased density and/or increased release rate upon applying to the wound. Preferably, the particle size of the micronized particles is from about 0.05 µm to about 2 µm, from about 0.1 µm to about 1.0 µm, from about 0.2 µm to about 0.8 µm, from about 0.3 µm to about 0.7 µm, or from about 0.4 µm to about 0.6 µm. Alternatively, the particle size of the micronized particles is at least 0.05 µm, at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, or at least 1 µm. Alternatively, the particle size of the micronized particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, less than 0.1 µm, or less than 0.05 µm.

In one aspect, the initial micronization is performed by mechanical grinding or shredding. In another aspect, micronization is performed by cryogenic grinding. In this aspect, the grinding jar containing the tissue is continually cooled with liquid nitrogen from the integrated cooling system before and during the grinding process. Thus, the sample is embrittled and volatile components are preserved. Moreover, the denaturing of proteins in the amnion, intermediate tissue layer, and/or chorion is minimized or prevented. In one aspect, the CryoMill manufactured by Retsch can be used in this aspect.

The selection of components used to make the molded, dehydrated placental tissue graft described herein can vary depending upon the end-use of the placental tissue graft. For example, placental tissue or individual components such as amnion, chorion, intermediate tissue layer, Wharton's jelly or any combination thereof can be admixed with one another and subsequently micronized. In another aspect, one or more tissue grafts composed of one or more placental tissue, amnion, chorion, intermediate tissue layers, or any combination thereof (i.e., laminates) can be micronized. In a further aspect, one or more tissue grafts composed of one or more amnion, chorion, intermediate tissue layers, or any combination can be admixed with amnion, chorion, intermediate tissue layer, or any combination thereof as individual components and subsequently micronized.

The amount of different components can vary depending upon the application of the molded, dehydrated placental tissue graft. In one aspect, when the molded, dehydrated placental tissue graft is composed of amnion (with or without the intermediate tissue layer) and intermediate tissue layer, the weight ratio of amnion to intermediate tissue layer is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the molded, dehydrated placental tissue graft is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

Separation of particle sizes can be achieved by fractionation of the micronized material in sterile water by forming a suspension of particles. The upper most portion of the suspension will contain predominantly the smallest particles and the lower most portion of the suspension will contain predominantly the heaviest particles. Fractionation leads to particle size separation and repeated fractionation will lead to separation of the micronized particles into varying sizes. The so separated particles can be recombined in the desired ratio of particle size as is most appropriate for making the molded placental tissue graft and the desired medical application. As one skilled in the art would appreciate, different sizes of the particles result in different density and cohesive mass of the molded placental tissue graft, discussed below.

Preparation of Molded Placental Tissue Graft and
Pharmaceutical Compositions Thereof (Step 160)

The dehydrated micronized placental components, such as micronized amnion, chorion, intermediate tissue layer, and any combination thereof, when subjected to pressure preferably in a non-porous mold, form a desired shape and size defined by the mold. While a porous mold is less preferred, it is contemplated that such can be used in the methods of this invention if water or other solvents are allowed to escape during molding. The molded placental tissue graft has a sufficient density and cohesive mass to maintain its size and shape at least until the molded placental tissue graft is introduced to a subject. The cohesion of the molded placental tissue graft is determined, in part, by the particle size of the micronized placental components. For example, dehydrated micronized placental components having larger particle size require higher compressive pressure and/or longer compression time to obtain a molded placental tissue graft having the same density as that of a molded placental tissue graft composed of dehydrated micronized placental components having smaller particle size. In other words, for molded dehydrated placental tissue compositions obtained under the same compression condition, the compositions having larger particle size have less density and dissociate at a higher rate in comparison to the compositions having smaller particle size. Therefore, it is within the purview of one skilled in the art to optimize the particle size of the micronized placental components, thereby obtaining the molded placental tissue composition having a desired cohesiveness and desired end results when administered to a subject.

Optionally, one or more adhesives can be admixed with the micronized placental components prior to being introduced into the mold. Examples of such adhesives include, but are not limited to, fibrin sealants, cyanoacrylates, gelatin and thrombin products, polyethylene glycol polymer, albumin, and glutaraldehyde products. The adhesives used in the process should be dehydrated prior to being mixed with the micronized placental components such that the mixture of adhesives and micronized placental components has a sufficiently low water content to permit compression in a non-porous mold.

In addition to the placental tissue, amnion, the intermediate tissue layer, and chorion, additional dehydrated components can be added to the composition prior to and/or after micronization. In one aspect, a dehydrated filler can be added. Examples of fillers include, but are not limited to, allograft pericardium, allograft acellular dermis, purified xenograft Type-1 collagen, biocellulose polymers or copolymers, biocompatible synthetic polymer or copolymer films, purified small intestinal submucosa, bladder acellular matrix, cadaveric fascia, bone particles (including cancellous and cortical bone particles), or any combination thereof.

In another aspect, a dehydrated bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the molded, dehydrated placental tissue graft with bioactive agent to the region of interest, the bioactive agent is delivered to the region over time. Thus, the molded, dehydrated placental tissue graft described herein are useful as delivery devices of bioactive agents and other pharmaceutical agents when administered to a subject. Release profiles can be modified based on, among other things, the selection of the components used to make the molded placental tissue graft as well as the size of the particles contained in the placental tissue graft.

In yet another aspect, the micronized placental components are admixed with at least one plasticizer prior to compression or molding. One skilled in the art would select a suitable plasticizer, based on the biocompatibility of the plasticizer, effect of plasticizer on the degradation or erosion rate of the placental tissue graft in vivo, effect of the plasticizer on the properties of the mixture to facilitate the molding/compression process. Exemplary plasticizers included, but are not limited to, poly(ethylene glycol), glucosemonoesters and partial fatty acid esters, and the like.

In a further aspect, the in vivo degradation or erosion rate of the molded placental tissue composition, as well as the density and cohesiveness of the dehydrated micronized placental components, can be modified, for example, by cross-linking. The amnion can be cross-linked with the intermediate tissue layer, chorion, or a second amnion tissue. For example, a cross-linking agent can be added to the composition (e.g., amnion, chorion, intermediate tissue layer, or any combination thereof as individual components and/or as tissue grafts) prior to and/or after micronization. In general, the cross-linking agent is nontoxic and non-immunogenic. When the amnion, intermediate tissue layer, and/or chorion (or a tissue graft thereof) are treated with the cross-linking agent, the cross-linking agent can be the same or different. In one aspect, the amnion, intermediate tissue layer, and chorion can be treated separately with a cross-linking agent or, in the alternative, the amnion, intermediate tissue layer, and chorion can be treated together with the same cross-linking agent. In certain aspects, the amnion, intermediate tissue layer, and chorion can be treated with two or more different cross-linking agents. The conditions for treating the amnion, intermediate tissue layer, and chorion can vary. In other aspects, the amnion, intermediate tissue layer, and/or chorion can be micronized, and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. Preferably, the placental tissue components are cross-linked prior to dehydration such that the cross-linked placental tissue components have a sufficiently low water content to permit compression or molding in a non-porous mold.

In certain aspects, the molded, dehydrated placental tissue composition can be treated with the cross-linking agent. Preferably, the placental tissue graft is subjected to gas/fume cross-linking prior to compression and before or after micronization such that the water content of the placental tissue component is maintained at a low level, e.g., less than about 20%, less than about 15%, less than about 10%, or less than about 5%. The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy]succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), ethylene glycol diglycidyl ether (EGDE), nordihydroguaiaretic acid (NDGA).

In one aspect, sugar is the cross-linking agent, where the sugar can react with proteins present in the amnion, intermediate tissue layer, and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentiobiose, melibiose, turanose, trehalose, isomaltose, or any combination thereof.

The pharmaceutical compositions described herein can be administered in a number of ways depending on whether local or systemic treatment is desired, and on the area to be treated. In one aspect, administration can be by injection. In other aspects, the molded dehydrated placental tissue composition can be formulated to be applied internally to a subject. In other aspects, the molded dehydrated placental tissue composition can be applied topically, subdermally or subcutaneously.

III. Applications of Compositions Comprising Molded Micronized Placental Components The compositions comprising molded dehydrated micronized placental components described herein have numerous medical applications. For example, the molded, dehydrated placental tissue composition may be administered or implemented locally to a tendon, a cartilage, heart muscle, ulcer or lesion without incision to the skin.

The molded dehydrated placental tissue compositions described herein are particularly useful as a filler. In this aspect, the molded dehydrated placental tissue composition is useful in filling a void or hole in a subject in order to enhance wound healing. The void or hole may be due to an injury or a wound. Alternatively, the void or hole may be generated by surgery or drilling such as laser drilling. During surgery, the molded dehydrated placental tissue composition can be used as a filler being applied between tissues, bones, or other body parts. One skilled in the art would understand that a void or hole can be drilled in a subject such that a molded placental tissue composition can be applied to the desired treatment area.

In other aspects, the molded dehydrated placental tissue compositions are effective in healing dermal wounds, where the wound is present in the dermis and/or subdermis. Thus, the molded dehydrated placental tissue compositions are effective in treatment of deep skin wounds. The source of the dermal wound can vary. In one aspect, the molded dehydrated placental tissue compositions can be used to heal an acute, open wound including, but not limited to, an incision, a laceration, an abrasion, a puncture, or a burn. In other aspects, the molded dehydrated placental tissue compositions can be used to heal a chronic wound such as a diabetic ulcer, a venous ulcer, or a pressure ulcer.

The molded dehydrated placental tissue compositions are particularly useful in non-load void filling, especially where it is desirable to have a product that will conform to irregular shapes. The pre-formed shape and size of the molded dehydrated placental tissue composition can maximize the contact area with the surface intended for treatment, thereby improving the therapeutic effects.

In addition to void filling, one skilled in the art would understand that the compositions described herein can also be used in a hole drilled in a body part such that the compositions can reach the intended treatment area. Therefore, the compositions of the invention are useful in wound covering and wound healing in general, especially for urgent care of acute wounds.

In other aspects, the molded dehydrated placental tissue composition can be used in combination with any other placental tissue products. For example, one or more placental tissues such as, for example, a layer of amnion, chorion, or a laminate of amnion and/or chorion can be affixed to the molded placental tissue composition. In this aspect, the molded placental tissue composition can be inserted into a wound or void, where an amnion, chorion, or laminated layer is on the outside of the wound and holds the molded placental tissue composition in place, much like a bandage.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preparation of Micronized Composition

Example 1

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding Dewar. Tissue samples were subjected to vapor phase cooling for no more than 30-60 minutes. The Cryo-rack was removed from the Dewar, and the Cryo-block was removed from the Cryo-rack. The Cryo-block was placed into the Grinder (SPEX Sample Prep GenoGrinder 2010) and set at 1,500 rpm for 20 minutes. After 20 minutes has elapsed, the tissue is inspected to ensure micronization. If necessary, the tissue can be placed back into the Dewar for an additional 30-60 minutes, and moved to the grinder for an additional 20 minutes to ensure sufficient micronization. Once the tissue is sufficiently micronized it is sorted using a series of American Standard ASTM sieves. The sieves were placed in the following order: 355 µm, 300 µm, 250 µm, 150 µm, and 125

µm. The micronized material was transferred from the 50 mL vials to the 355 µm sieve. Each sieve was agitated individually in order to thoroughly separate the micronized particles. Once the micronized particles have been effectively separated using the sieves, the micronized particles having particle sizes of 355 µm, 300 µm, 250 µm, 150 µm, and 125 µm were collected in separate vials.

Preparation of Molded Placental Tissue Composition Comprising Micronized Particles Example 2

A mold having a female half and a male half in a crescent moon shape is used in preparing molded dehydrated placental tissue composition. The female half is loaded with 10 mg micronized amnion/chorion particles prepared in Example 1. Once the male half is in place to contain the microparticles, the mold is subjected to a suitable pressure for a suitable period of time to obtain the molded placental tissue composition having the size and shape of the mold.

In one embodiment, the mold is a non-porous mold and the water content of the dehydrated placental tissue is less than about 25% weight/weight. In another embodiment, the water content is greater 25% weight/weight and a porous mold is used to allow excess water to be removed. Alternatively, a small volume (e.g. 10 weight percent or less) of a biocompatible organic solvent can be added to the dehydrated placental tissue so that during compression, the solvent vaporization will lead to small voids within the composition.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in U.S. Provisional Patent Application No. 61/683,697 filed on Aug. 15, 2012, which application is incorporated herein by reference in its entirety.

A detailed description of micronized placental tissue is provided in U.S. Provisional Patent Application Nos. 61/683,698 and 61/683,700, both filed on Aug. 15, 2012, which applications are incorporated herein by reference in their entireties.

What is claimed:

1. A molded, compressed, dehydrated placental tissue composition having a defined size and shape wherein said molded dehydrated placental tissue composition consists essentially of washed, cleaned, micronized amnion, and optionally one or more of washed, cleaned, micronized chorion, intermediate tissue layer, additional amnion, and any combination thereof, wherein at least one of the amnion comprises a fibroblast cell layer, and wherein said composition has a sufficient density and cohesiveness to maintain its size and shape for a defined period of time ex vivo and in vivo, wherein the density of the composition is from 1.2 g/cm$^3$ to 10 g/cm$^3$; and wherein the water content of the composition is less than 5%.

2. The composition of claim 1, wherein the micronized amnion, chorion, intermediate tissue layer, and any combination thereof has a particle size of less than 400 µm.

3. The composition of claim 1, wherein at least one of the amnion, chorion, intermediate tissue layer, or any combination thereof are cross-linked.

4. A pharmaceutical composition comprising the composition of claim 1 and optionally a pharmaceutically acceptable excipient.

5. The composition of claim 1, wherein the micronized amnion, chorion, intermediate tissue layer, and any combination thereof has a particle size of less than 350 µm.

6. The composition of claim 1, wherein the micronized amnion, chorion, intermediate tissue layer, and any combination thereof has a particle size of less than 300 µm.

7. A molded, compressed, dehydrated placental tissue composition having a defined size and shape, wherein said composition consists of washed, cleaned, micronized amnion wherein the amnion comprises a fibroblast cell layer, wherein said composition has a sufficient density and cohesiveness to maintain its size and shape for a defined period of time ex vivo and in vivo wherein the density is from 1.2 g/cm$^3$ to 10 g/cm$^3$; and wherein the composition has a water content which is less than 5%.

8. The composition of claim 7, wherein the micronized amnion has a particle size of less than 400 µm.

9. The composition of claim 7, wherein the micronized amnion has a particle size of less than 350 µm.

10. The composition of claim 7, wherein the micronized amnion has a particle size of less than 300 µm.

11. A molded, compressed, dehydrated placental tissue composition having a defined size and shape, wherein said composition consists of washed, cleaned, micronized amnion and washed, cleaned, micronized chorion, wherein the amnion comprises a fibroblast cell layer, wherein said composition has a sufficient density and cohesiveness to maintain its size and shape for a defined period of time ex vivo and in vivo wherein the density is from 1.2 g/cm$^3$ to 10 g/cm$^3$; and wherein the composition has a water content which is less than 5%.

* * * * *